United States Patent [19]

Cooper

[11] Patent Number: 4,835,108

[45] Date of Patent: May 30, 1989

[54] METHOD FOR MEASURING FREE OXYGEN IN A COMBUSTIBLE ATMOSPHERE

[75] Inventor: Marshall H. Cooper, Solon, Ohio

[73] Assignee: The Babcock & Wilcox Company, New Orleans, La.

[21] Appl. No.: 109,808

[22] Filed: Oct. 16, 1987

Related U.S. Application Data

[62] Division of Ser. No. 891,075, Jul. 28, 1986.

[51] Int. Cl.$^4$ .............................................. G01N 33/22
[52] U.S. Cl. .................................... 436/137; 436/143; 422/94; 422/98
[58] Field of Search .................. 436/137, 143; 422/94, 422/98; 338/34

[56] References Cited

U.S. PATENT DOCUMENTS

| | | | |
|---|---|---|---|
| 1,321,063 | 11/1919 | Lamb et al. | 436/143 |
| 1,779,569 | 10/1930 | Thompson | 436/143 |
| 2,298,288 | 10/1942 | Gerrish et al. | 436/137 |
| 2,531,592 | 11/1950 | Yant et al. | 436/143 |
| 3,480,397 | 11/1969 | Baumgartel | 436/137 |
| 3,607,084 | 9/1971 | Mackey et al. | 436/143 |
| 3,960,500 | 6/1976 | Ross et al. | 422/62 |
| 4,063,898 | 12/1977 | Fisher | 436/141 |
| 4,134,818 | 1/1979 | Pebler et al. | 436/137 |

Primary Examiner—David L. Lacey
Assistant Examiner—L. Johnson
Attorney, Agent, or Firm—Vytas R. Matas; Robert J. Edwards

[57] ABSTRACT

A detector for measuring free oxygen at ambient temperature in a combustible atmosphere which may be hazardous constructed as a differential thermocouple pair with the first thermocouple junction coated with a catalyst and the second thermocouple junction coated with a non-catalyst. Free oxygen in the combustible atmosphere reacts with the catalyst to liberate heat and thereby raise the temperature of the catalyst coated junction above that of the non-catalyst coated junction. Thus, the increase in temperature of the first thermocouple above that of the second thermocouple is indicative of the free oxygen in the combustible atmosphere.

7 Claims, 4 Drawing Sheets

METHOD FOR MEASURING FREE OXYGEN IN A COMBUSTIBLE ATMOSPHERE

This is a division of application Ser. No. 891,075, filed July 28, 1986.

BACKGROUND OF THE INVENTION

(1) FIELD OF THE INVENTION

The present invention relates in general to oxygen detectors and in particular to a differential thermocouple device adapted to measure free oxygen in a combustible atmosphere.

(2) DESCRIPTION OF THE PRIOR ART

Oxygen detectors are known which utilize an oxygen ion condutive solid electrolyte, such as zirconium oxide, to sense oxygen content in process gases and combustion flue gases. A system utilizing such a sensor is illustrated in U.S. Pat. No. 3,960,500 issued to Ross et al. Such sensors require elevation of the sensor temperature to its active zone in order to provide a signal indicative of the oxygen content in the gas sample. The required sensor operating temperature may be in excess of 1500F. Obviously this type of sensor is unsuitable for detecting free oxygen in a combustible atmosphere since its operating temperature would be in excess of the auto-ignition temperature of the combustible atmosphere. In addition, the high operating temperature of such sensors could cause the free oxygen to react with the combustible atmosphere prior to actually being detected thereby resulting in a lower, false indication of free oxygen in the combustible atmosphere. This false indication may result in potentially dangerous levels of free oxygen in the combustible atmosphere going undetected.

Prior differential thermocouples detector, such as illustrated in U.S. Pat. No. 4,063,898 issued to Fisher, have been used to monitor combustible gases in an airstream. Such detectors include a differential thermocouple pair with one junction coated with a catalyst and the other junction with a non-catalyst. Combustible gases are heated above the existing ambient temperature of the atmosphere to react with the catalyst to liberate heat to the catalyst-coated thermocouple junction thereby raising the temperature of the catalyst-coated junction above that of the non-catalyst coated junction in proportion the concentration of combustible gases. The output signal from such a device is thus indicative of the concentration of combustible gases in the airstream. However, the applicant is unaware of any prior art combustibles detectors using such differential thermocouples being adapted to measure free oxygen in a combustible atmosphere at the existing ambient temperature of the atmosphere.

It has thus become desirable to develop a detector that will monitor free oxygen in a combustible atmosphere while at the same time eliminating the prior art problem of high sensor operating temperatures that may be excess of the auto-ignition temperature of the combustible atmosphere or result in a false indication of the free oxygen level in the combustible atmosphere.

SUMMARY OF THE INVENTION

The present invention solves the aforementioned problems associated with the prior art by providing a differential thermocouple device for measuring free oxygen in a combustible atmosphere which operates at a temperature below the auto-ignition temperature of the combustible atmosphere. A first thermocouple junction of a thermocouple pair is coated with a catalyst material to allow free oxygen in a combustible atmosphere to react with the catalyst to liberate heat and thereby raise the temperature of the catalyst coated thermocouple junction. The second thermocouple junction of the thermocouple pair is coated with a non-catalyst material to prevent free oxygen in the combustible atmosphere from reacting with the second thermocouple junction to liberate heat. Thus, the increase in temperature of the first thermocouple above that of the second thermocouple is proportional to the free oxygen in the combustible atmosphere.

Accordingly, one aspect of the present invention is to provide a detector for measuring free oxygen in a combustible atmosphere that is operable without any external heat application.

Another aspect of the present invention is to provide a detector for measuring free oxygen in a hazardous atmosphere that is inherently safe.

Still another aspect of the present invention is to provide an analyzer for detecting free oxygen in a combustible atmosphere which utilizes a differential thermocouple.

These and other aspects of the present invention will be more clearly understood after a review of the following description of the preferred embodiment of the invention when considered with the drawings.

DESCRIPTION OF THE PREFERRED EMBODIMENTS

Figure 1:
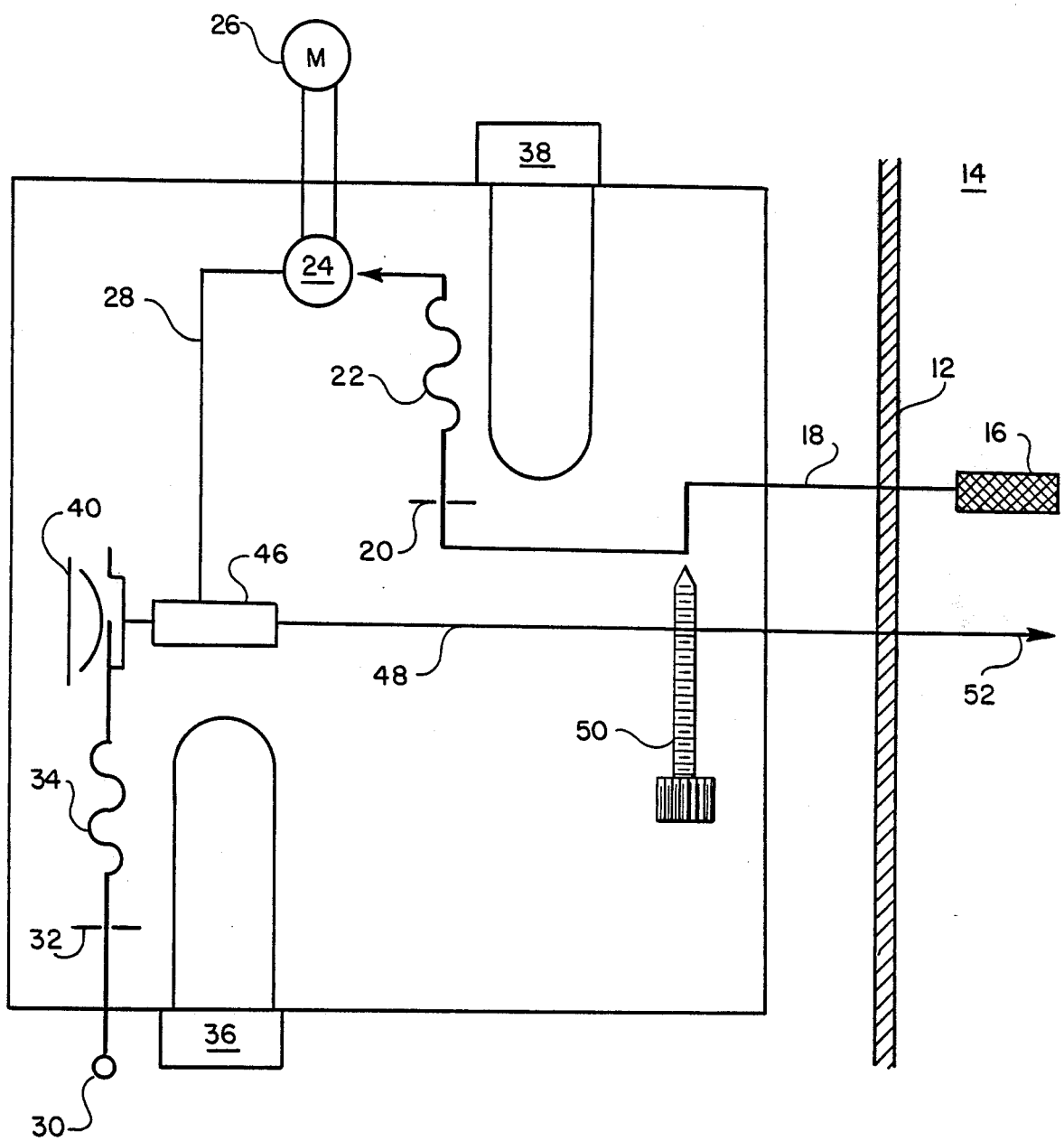
FIG. 1 is a schematic illustration of the present invention.

Referring now to the drawings, it will be understood that the illustrations are for the purpose of describing a preferred embodiment of the invention and are not intended to limit the invention thereto.

As may be best seen with reference to FIG. 1, a sampling analyzing assembly, generally designated 10, is connected to an annealing furnace wall 12 to draw a sample of a combustible atmosphere 14 from inside the annealing furnace for analysis and exhaust it back into the same furnace through an exhaust line 48 to prevent condensation at exhaust outlet 52. The sampling analyzing assembly 10 may be similar to the system described in U.S. Pat. No. 3,960,500 which provides for recirculation of flue gases from a duct and back thereto. Further details of such a sampling analyzing system are available in the above-referenced patent and the reader is referred thereto for any further required clarification.

The sample of the combustible atmosphere 14 is drawn into the sampling analyzing assembly 10 through a sample probe 16 which extends into the annealing furnace. The probe 16 may be similar to that described in U.S. Pat. No. 4,286,472 and serves to prevent dust and soot particles from being entrained by the probe 16 and therefrom into the sampling analyzing assembly 10. Further details of such a probe are available in the above-referenced patent and the reader is referred therto for any further required clarification.

The sample of the combustible atmosphere 14 is drawn into the sampling analyzing assembly 10 through the probe 16 by the action of an aspirator assembly 46. The aspirator assembly 46 is powered by aspirating gas provided by an aspirating gas supply 30 which in the preferred embodiment is a tank pressurized nitrogen gas but other gases, mixtures thereof, or shop air may be substituted depending on the composition of the combustible atmosphere 14 and whether the sample of the combustible atmosphere 14 is exhausted back into the annealing furnace or to the atmosphere. A conventional pressure regulator (not shown) is connected to the aspirating gas supply 30 in order to maintain the outlet pressure of the aspirating gas at approximately 15 PSI.

The aspirating gas supply 30 is connected to an aspirating gas orifice 32 which is sized with respect to the outlet pressure of the aspirating gas supply 30 and the action of the aspirator assembly 46 to provide a total sampling rate of the combustible atmosphere 14 of between 1425 and 2375 cc/min with 1900 cc/min being the preferred sampling rate.

The aspirating gas orifice 32 is connected to the aspirator assembly 46 by a connecting line 34 which is formed within the sampling analyzing assembly 10 as a series of sinusoidal paths. The connecting line 34 is made sinusoidal to provide a longer contact time with the aspirating gas in order to pre-condition the aspirating gas before it contacts the aspirator assembly 46. A resistance heater/thermostat assembly 36 is located adjacent to the connecting line 34 and is thermostatically controlled to maintain the temperature of the aspirating gas above the dewpoint of the combustible atmosphere 14 thereby preventing condensation from occuring with the drawn sample of combustible atmosphere 14 when the two are mixed in the aspirator assembly 46.

A temperature-actuated flow control device 40 is connected between the aspirator assembly 46 and the connecting line 34. The flow control device 40 may be similar to that described in U.S. Pat. No. 4,557,419 issued to Hall and serves to permit the continuous sampling of the combustible atmosphere 14 above the dewpoint of the combustible atmosphere 14 and to stop the sampling of the combustible atmosphere 14 by the sampling analyzing system 10 whenever the temperature of the aspirating gas falls below the dewpoint of the combustible atmosphere 14. Further details of such a temperature-actuated flow control device are availble in the above-referenced patent and the reader is referred thereto for any further required clarification.

The probe 16 is connected via a sample inlet line 18 to a sample orifice 20 which also is sized with respect to the outlet pressure of the main gas supply 30 and the action of the aspirator assembly 46 to provide a total sampling rate of the combustible atmosphere 14 of between 1425 and 2375 cc/min with 1900 cc/min being the preferred sampling rate.

The sample orifice 20 is connected to a connecting line 22 which is formed within the sampling analyzing assembly 10 as a series of sinusoidal paths in the same manner as the connecting line 34, discussed above, in order to pre-condition the gas sample before it contacts the sensor assembly 24 and the aspirator assembly 46. A resistance heater/thermostat assembly 38 is located adjacent to the connecting line 22 and is thermostatically controlled to maintain the temperature of the sample of the combustible atmosphere 14 above its dewpoint thereby preventing condensation from occuring within the connecting line 22 or sensor assembly 24.

Figure 3:
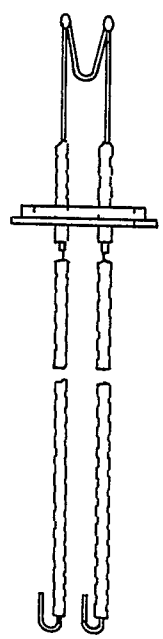
FIG. 3 is a side view of the differential thermocouple sensor utilized by the present invention.

The connecting line 22 is connected to a sensor assembly 24. The sensor assembly 24 serves to permit the continuous analysis of the combustible atmosphere 14. The sensor assembly 24 may include a differential thermocouple detector similar to that described in U.S. Pat. No. 4,063,898 and as shown in FIG. 3. The detector includes a differential thermocouple pair with one junction coated with a catalyst and the other junction with a non-catalyst. Further details of such a detector are available in the above-referenced patent and the reader is referred thereto for any further required clarification.

The sample of the combustible atmosphere 14 reacts with the catalyst to liberate heat to the catalyst-coated thermocouple junction thereby raising the temperature of the catalyst-coated junction above that of the non-catalyst coated junction in proportion to the concentration of free oxygen in the combustible atmosphere 14. A voltmeter 26 is connected to the sensor assembly 24 to provide a display of the output of the sensor assembly 24.

Figure 2A:
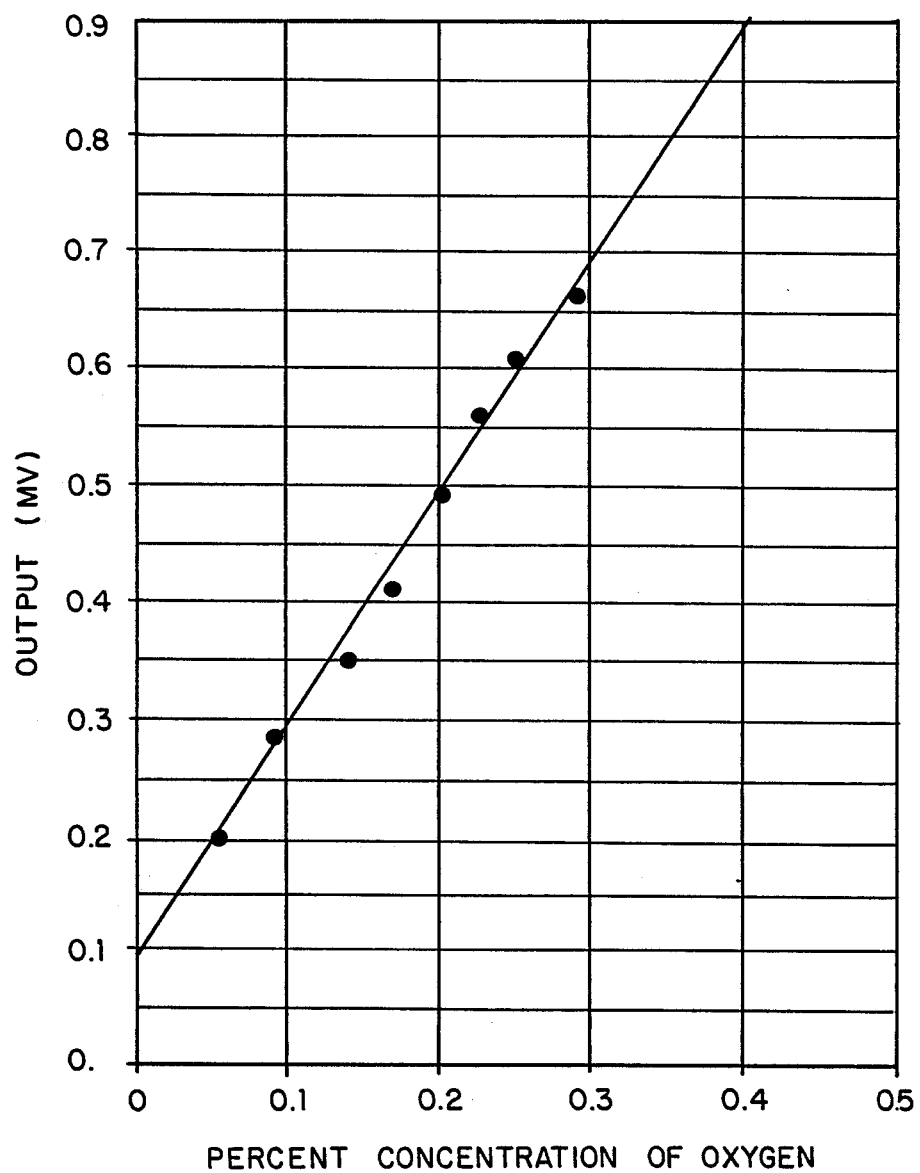
FIG. 2a and 2b are graphical illustrations of the sensor output (millivolts) v. oxygen concentration of the differential thermocouple sensor of the present invention.
Figure 2B:
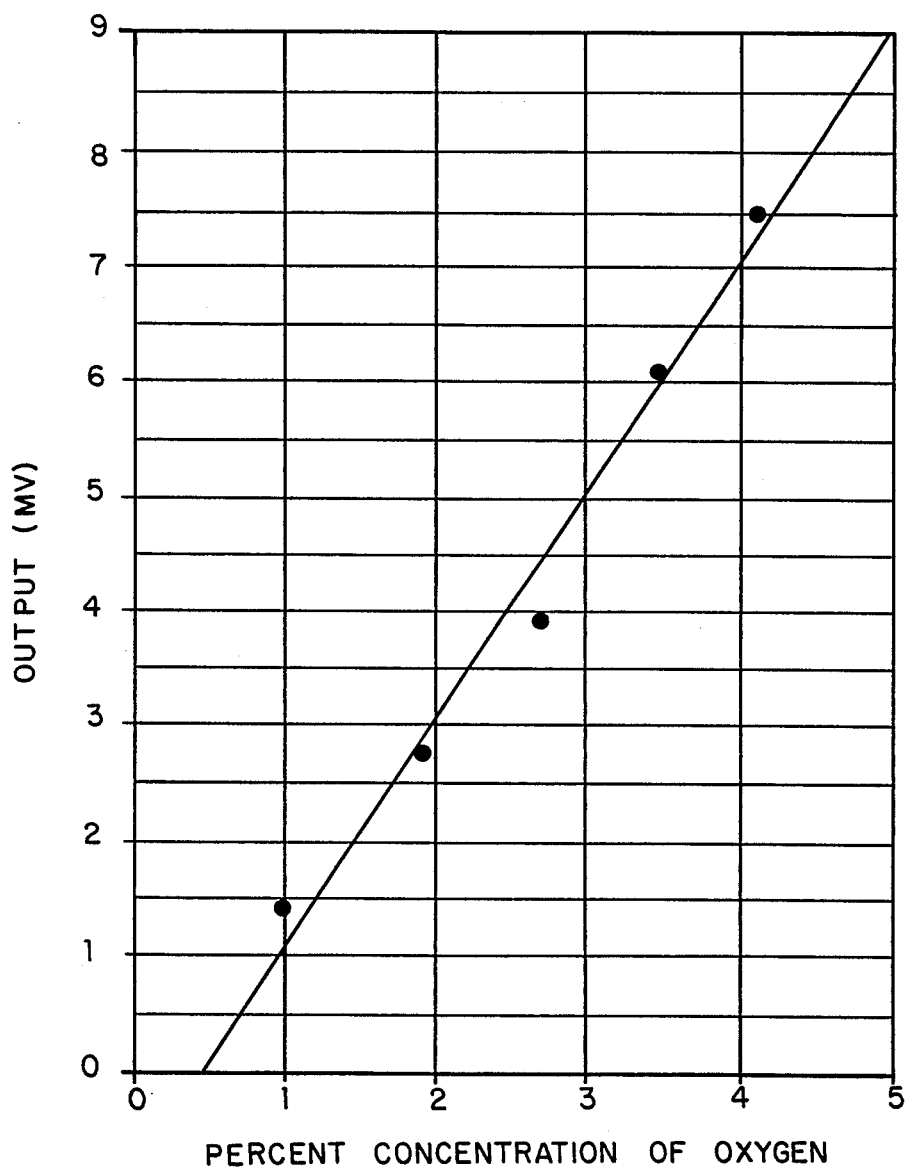

Referring to FIGS. 2a and 2b, it may be seen that varying concentrations of free oxygen will produce a corresponding variable mullivolt output at the voltmeter 26 as a result of the heat liberated to the catalytic-coated thermocouple junction depending on the concentration of free oxygen in the combustible atmosphere 14. The output signal from the sensor assembly 24 is thus indicative of the concentration of free oxygen in the combustible atmosphere 14. The voltmeter 26 may be calibrated according to the chart disclosed in FIG. 2 to provide a direct readout of the concentration of free oxygen in the sample of the combustible atmosphere 14 passing through the sensor assembly 24.

An outlet line is connected between the sensor assembly 24 and the aspirator asembly 46 to receive the sample of combustible atmosphere 14 from the sensor assembly 24. The sample if then exhausted through the exhaust line 48 and out at the exhaust outlet 52 either back into the same furnace or to the atmosphere.

A shut-off valve 50 located inline with the sample inlet line 18 allows manual closing of the sample inlet line 18 thereby isolating the sampling analyzing assembly 10 to permit routine calibration and maintenance of the sampling analyzing assembly 10.

Certain modifications and improvements will occur to those skilled in the art upon reading of the foregoing description. By way of example, the detector shown in FIG. 3 may include an additional catalyst coated thermocouple junction and an additional non-catalyst coated thermocouple junction connected in series thereby doubling the sensitivity of the detector to free oxygen. It should be understood that all such modifications and improvements have been deleted herein for the sake of conciseness and readability but are properly within the scope of the following claims.

We claim:

1. A method of detecting free oxygen in a combustible atmosphere at a temperature below the auto-ignition temperature of the atmosphere comprising:
    providing an oxygen sensor;
    providing a combustible atmosphere below the auto-ignition temperature thereof but above the dewpoint thereof to said sensor; and
    measuring free oxygen in said atmosphere at the provided temeprature with said sensor without any external heat application to said sensor.

2. A method according to claim 1, wherein said sensor comprises a first thermocouple junction located in the combustible atmosphere; and catalytic means formed around said first thermocouple junction allowing free oxygen in the combustible atmosphere to react with said catalytic means to liberate heat and thereby increase the temperature of said first thermocouple, said increase in temperature being proportional to the free oxygen in the combustible atmosphere.

3. A method accoridng to claim 2, wherein said sensor further comprises a second thermocouple junction located in the combustible atmosphere; and means for preventing free oxygen in said combustible atmosphere from reacting with said second thermocouple junction to liberate heat.

4. A method of measuring free oxygen in a hazardous atmosphere in an inherently safe manner comprising:
providing an oxygen sensor;
providing a hazardous atmosphere at a temperature below the auto-ignition temperature but above the dewpoint of the hazardous atmosphere to said sensor; and
measuring free oxygen in said hazardous atmosphere at the existing temperature of the hazardous atmosphere with said sensor without the application of external heat to said sensor.

5. A method according to claim 4, wherein said sensor further comprises a first thermocouple junction located in the hazardous atmosphere;
a second thermocouple junction located in the hazardous atmosphere; and
catalytic means formed around said first thermocouple junction allowing free oxygen in the hazardous atmosphere to react with said catalytic means to liberate heat and thereby create a temperature differential between said first thermocouple above that of said second thermocouple, said temperature differential being proportional to the free oxygen in the hazardous atmosphere.

6. A method according to claim 5, wherein said first thermocouple is connected to said second thermocouple to form a differential thermocouple.

7. A method according to claim 5, including indicating the temperature differential between said first and second thermocouple junctions.

* * * * *